(12) United States Patent
Dever et al.

(10) Patent No.: US 6,227,458 B1
(45) Date of Patent: May 8, 2001

(54) DEODORIZER

(75) Inventors: Gerald R. Dever, Cordova; Thomas J. Laughlin, Germantown; William S. Rogers, Cordova, all of TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 0 days.

(21) Appl. No.: 08/162,508

(22) Filed: Dec. 3, 1993

(51) Int. Cl.[7] .................................................. A24F 25/00
(52) U.S. Cl. ........................... 239/36; 424/76.4; 36/71; 36/1; 36/91
(58) Field of Search ............... 424/76.4; 239/36, 239/34; 36/71, 1, 91

(56) References Cited

U.S. PATENT DOCUMENTS

| | | |
|---|---|---|
| 2,973,286 | 2/1961 | Ulrich . |
| 3,655,129 | 4/1972 | Seiner . |
| 3,685,734 | 8/1972 | Paciorek et al. . |
| 4,051,159 | 9/1977 | Tsoucalas et al. . |
| 4,161,284 | 7/1979 | Rattan ................................... 239/43 |
| 4,283,011 | 8/1981 | Spector ................................. 239/36 |
| 4,284,444 | 8/1981 | Bernstein et al. . |
| 4,316,333 * | 2/1982 | Rothschild ............................. 36/91 |
| 4,419,396 | 12/1983 | Sugimoto . |
| 4,493,869 | 1/1985 | Sweeny et al. . |
| 4,605,592 | 8/1986 | Paquette et al. . |
| 4,654,256 | 3/1987 | Doree et al. . |
| 4,694,590 | 9/1987 | Greenawalt . |
| 4,696,844 | 9/1987 | Spector . |
| 4,701,536 | 10/1987 | Klingen et al. . |
| 4,714,655 | 12/1987 | Bordoli et al. . |
| 4,720,409 | 1/1988 | Spector . |
| 4,735,010 | 4/1988 | Grinarml . |
| 4,737,410 | 4/1988 | Kantner . |
| 4,749,590 | 6/1988 | Klingen et al. . |
| 4,774,133 | 9/1988 | Doree et al. . |
| 4,813,157 * | 3/1989 | Boisvert et al. ....................... 36/91 |
| 4,814,212 | 3/1989 | Spector . |
| 4,841,648 * | 6/1989 | Shaffer et al. ......................... 36/91 |
| 4,874,129 | 10/1989 | DiSapio et al. . |

(List continued on next page.)

FOREIGN PATENT DOCUMENTS

| | | |
|---|---|---|
| C 451 950 | 10/1927 | (DE) . |
| U 17 18 084 | 10/1955 | (DE) . |
| 32 33 006 A1 | 3/1984 | (DE) . |
| 35 16 653 A1 | 11/1986 | (DE) . |
| 0103407 A1 | 3/1984 | (EP) . |
| 0213737 A1 | 7/1986 | (EP) . |
| 0 272 690 A2 | 6/1988 | (EP) . |
| 0 300 084 A2 | 1/1989 | (EP) . |
| 1455904 | 10/1966 | (FR) . |
| 2 183 479 | 6/1987 | (GB) . |
| WO 79/01013 | 11/1979 | (WO) . |
| WO 89/07429 | 8/1989 | (WO) . |
| WO 90/04339 | 5/1990 | (WO) . |

OTHER PUBLICATIONS

Robert T. Maleeny and William F. Palmer, Environmental Odor Control, Soap/Cosmetics/Chemical Specialties for Jan. 1991, pp. 28–31.

F. Kanda, et al.,BritishJournalof Dermatology, 122, (1990), pp. 771–776.

The Handbook of Water–Soluble Gums and Resins by Robert L. Davidson, Chapter 21—"Polyvinylpyrrolidone", McGraw–Hill, Inc. (1980), pp. 21–1 to 21–21.

Awear product specifications sheet by Thermedics Inc., 470 Wildwood Street P.O. Box 2999, Woburn, Massachusetts, 2 pages.

*Primary Examiner*—Robert H. Harrison
(74) *Attorney, Agent, or Firm*—Henry S. Hadad; Robert J. Lipka

(57) ABSTRACT

A deodorizer for masking foot and shoe odors through controlled release of fragrance and which utilizes releasable interlocking surfaces for retaining the deodorizer in contact with the shoe is claimed.

12 Claims, 3 Drawing Sheets

U.S. PATENT DOCUMENTS

| | | |
|---|---|---|
| 4,880,690 | 11/1989 | Szycher . |
| 4,889,755 | 12/1989 | Charbonneau . |
| 4,898,633 | 2/1990 | Doree et al. . |
| 4,943,461 | 7/1990 | Karim . |
| 4,959,208 | 9/1990 | Chakrabarti et al. . |
| 5,154,682 * | 10/1992 | Kellerman ................................ 36/71 |
| 5,372,303 * | 12/1994 | Paul ....................................... 239/56 |
| 5,395,047 * | 3/1995 | Pendergrass, Jr. ..................... 239/56 |
| 5,399,404 * | 3/1995 | Laughlin et al. .................... 428/41.3 |
| 5,492,675 * | 2/1996 | Brizard ................................. 422/122 |
| 5,569,683 * | 10/1996 | Bootman et al. ..................... 523/102 |
| 5,732,485 * | 3/1998 | Laughlin et al. ....................... 36/136 |
| 5,738,831 * | 4/1998 | Bethel ................................. 422/120 |
| 5,782,408 * | 7/1998 | Carter ..................................... 239/34 |
| 5,829,167 * | 11/1998 | Valenzuela ............................. 36/3 B |

* cited by examiner

DEODORIZER

BACKGROUND

According to Robert T. Maleeny and William F. Palmer, Environmental Odor Control, Soap/Cosmetics/Chemical Specialties for January 1991, pp. 28–31, malodors are usually caused by chemicals that are perceived at very low concentrations. Although malodors may not be dangerous to health at low levels, they can affect one's enjoyment of the environment. Maleeny and Palmer disclose that the perfumers of ancient Egypt and Medieval Europe practised masking by deodorizing through the use of perfumes, colognes and sachets. The authors also suggested that foot care can be one of many applications for malodor counteractants. However, there are few, if any commercially available perfume deodorizers in which the perfume component of the deodorizer can be releasably attached to and removed from the interior of a shoe, and still provide sufficient perfume to mask foot or shoe odors. Part of the problem of constructing such a deodorizer lies in the relatively high loading of fragrance in the component containing the perfume (ie. about 10 milligrams (mg) or greater) necessary to mask the foot and shoe odors. Such concentrated loadings of fragrance in the perfume component can cause the adhesive holding the deodorizer to the footwear to soften, causing the deodorizer to loosen from the footwear. In view of the foregoing, it would be desirable to provide a convenient deodorizer for masking foot and shoe odors in which the perfume component could be easily applied to and removed from the shoe interior. It would also be desirable to provide a deodorizer for masking foot and shoe odors through controlled release of fragrance.

SUMMARY OF THE INVENTION

In a first embodiment, the present invention is directed toward a deodorizer for masking foot and shoe odors, comprising:
  a) a patch containing fragrance in amounts effective to mask foot and shoe odors;
  b) a fastener having means for securing said fastener to the interior surface of a shoe; and
  c) means attached to said fragrance containing patch and means attached to said fastener providing releasable interlocking surfaces which engage upon pressing together said interlocking surfaces of said patch and said fastener and release upon pulling said surfaces apart.

In a more limited embodiment, the means providing a releasable interlocking surface for said fragrance-containing patch is a surface containing loops or fibrous material and the means providing a releasable interlocking surface for said fastener contains velcro hooks for interlocking with said loop or fibrous material of said fragrance-containing patch.

In a second embodiment, the means providing a releasable interlocking surface for said fragrance-containing patch is a surface containing velcro hooks and the means providing a releasable interlocking surface for said fastener contains loop or fibrous material for interlocking with said velcro hooks of said fragrance-containing patch.

In another embodiment, the present invention is directed towards a deodorizer for masking foot and shoe odors, comprising:
  a) a patch containing fragrance in amounts effective to mask foot and shoe odors;
  b) a retaining ring having an opening into which said fragrance-containing patch is inserted into and said retaining ring also having means for securing said fastener to the interior surface of a shoe;
  c) a cap for maintaining said patch within said retaining ring; and
  d) means attached to said retaining ring and means attached to said cap providing releasable interlocking surfaces which engage upon pressing together said interlocking surfaces of said retaining ring and said cap and release upon pulling said surfaces apart.

In a more limited embodiment, the means providing a releasable interlocking surface for said retaining ring is a surface containing velcro hooks and the means providing a releasable interlocking surface for said cap contains loop or fibrous material for interlocking with said velcro hooks of said retaining ring.

In another more limited embodiment, the means providing a releasable interlocking surface for said retaining ring is a surface containing loops or fibrous material and the means providing a releasable interlocking surface for said cap contains velcro hooks for interlocking with said loop or fibrous material of said retaining ring.

In a third embodiment, the present invention is directed toward a method for deodorizing foot and shoe odors comprising attaching to the interior of a shoe the deodorizer comprising:
  a) a patch containing fragrance in amounts effective to mask foot and shoe odors;
  b) a fastener having means for securing said fastener to the interior surface of a shoe; and
  c) means attached to said fragrance containing patch and means attached to said fastener providing releasable interlocking surfaces which engage upon pressing together said interlocking surfaces of said patch and said fastener and release upon pulling said surfaces apart.

In a fourth embodiment, the present invention is directed toward a method for deodorizing foot and shoe odors comprising attaching to the interior of a shoe the deodorizer comprising:
  a) a patch containing fragrance in amounts effective to mask foot and shoe odors;
  b) a retaining ring having an opening into which said fragrance-containing patch is inserted into and said retaining ring also having means for securing said fastener to the interior surface of a shoe;
  c) a cap for maintaining said patch within said retaining ring; and
  d) means attached to said retaining ring and means attached to said cap providing releasable interlocking surfaces which engage upon pressing together said interlocking surfaces of said retaining ring and said cap and release upon pulling said surfaces apart.

Preferably, the deodorizer, including its components, ie. patch, fastener and cap are circular in shape. Also preferred is that the means for securing said fastener or said retaining ring to the interior of a shoe is a pressure-sensitive adhesive. In a more preferred embodiment, the fragranced patch is made of a carrier containing a mixture of fragrance and polymer binder. Preferably, the carrier is made of a non-woven felt, such as derived from polypropylene fibers. Also preferred is that the amount of fragrance in the patch ranges from about 10 milligrams or greater. Also preferred is that the polymer binder is polyvinylpyrrolidone.

The present invention has the advantage of masking undesirable odors in a shoe by the controlled release of fragrance lasting over a normal day's wear. A second advantage is that the controlled fragrance release can be triggered by moisture from the foot, thus minimizing fragrance loss from the patch prior to application to the foot or footwear, or during periods when the footwear is not in use. Where a felt carrier is employed, a third advantage of present invention is that it reduces the tackiness at the exposed surface of the fragrance patch. A fourth advantage of the present invention is that the patch containing the fragrance is easy to insert and remove with the need for little or no adhesive (other than the adhesive for securing the device to the shoe), since the deodorizer utilizes its loops/velcro hooks or a capped type construction to hold the patch in place. A fifth advantage of the present deodorizer is that it will stay secured to the footwear even when the deodorizer is moistened or wetted.

DESCRIPTION OF THE FIGURES

In the following drawings, FIGS. 1A–5A illustrate exploded top views of different embodiments for deodorizer 20 while FIGS. 1B–5B depict the components of deodorizer 20 as assembled for use.

In FIG. 1A and FIG. 1B, deodorizer 40 is made of fragrance containing patch 14, velcro hook-type fastener 2 and securing means 8. Patch 14 contains fragrance in amounts effective to mask foot and shoe odors. At least one surface 10 of patch 14 is made of a material sufficiently looping or fibrous to permit interlocking, intermeshing or mating with velcro hook-type fastener 2. Fragrance-containing patch 14 is held in place by interlocking or intermeshing surface 10 with surface 4 of velcro hook-type fastener 2. To the underside 6 of velcro hook-type fastener 2 is bonding means 8 (eg. pressure sensitive adhesive 8) for securing or anchoring fastener 2 to the interior surface of a shoe or other footwear. The adhesive secures retainer 2 to the interior surface of a shoe or other footwear. During packaging and storage of deodorizer 20, adhesive 8 is typically covered with a release liner, not shown. Optionally, patch 14 can also contain a tab 20 for facilitating attaching or removing patch 14 from velcro hook-type fastener 2. When the fragrance in patch 14 becomes depleted so that the patch is no longer effective, patch 14 can be easily removed from velcro hook-type fastener 2, for example, by prying with a fingernail or by lifting an edge or periphery 16 of patch 14, or by lifting optional tab 20. The used patch can be replaced with a fresh fragrance patch 14. Thus, patch 14 is releasably attached to velcro hook-type fastener 2.

In FIG. 2A and FIG. 2B, deodorizer 40 is made of fragrance containing patch 14a, velcro loop-type fastener 15, velcro hook-type fastener 2 and securing means 8. In this embodiment, deodorizer 20 differs from the deodorizer in FIGS. 1A and 1B by employing a fragrance containing patch 1 4a which is bonded on its underside to velcro loop-type fastener 15 having surface 10a for interlocking or mating with surface 4 of velcro hook-type fastener 2. Fragrance containing patch 14a can be bonded to velcro-loop type fastener 15 using any suitable adhesive or by sintering a surface of patch 14a with velcro-loop type fastener 15. Alternatively, a blend of the polymer and the fragrance can be coated on or impregnated into velcro-loop type fastener 15, thus eliminating the need for fragrance containing patch 14a.

In FIG. 3A and FIG. 3B, deodorizer 40 is made of fragrance containing patch 14a, velcro hook-type fastener 2, velcro loop-type fastener 15 and securing means 8. In this embodiment, deodorizer 20 primarily differs from the deodorizer in FIGS. 2A and 2B in that the positioning of the velcro fasteners is reversed. Fragrance containing patch 14a is bonded on its underside to velcro-hook type fastener 2 having surface 4 for interlocking or intermeshing with surface 10a of velcro loop-type fastener 15. Alternatively, a blend of the polymer and the fragrance can be coated on or impregnated into velcro-hook type fastener 2, thus eliminating the need for fragrance containing patch 14a.

In FIG. 5A and FIG. 5B, deodorizer 40 is made of velcro hook-type 25 cap 36, fragrance containing patch 14, velcro loop-type retaining ring 32 and securing means 8. In this embodiment, deodorizer 20 differs from the deodorizer in FIGS. 4A and 4B, primarily in that the positioning of the hook and loop portions of the velcro fasteners is reversed. Fragrance containing patch 14 is inserted into interior 30 of velcro loop-type retaining ring 32, and velcro hook-type cap 36 is placed atop velcro loop-type retaining ring 32, with cap 36 and ring 32 intermeshing at corresponding velcro hooks 39 and loop-type surface 34. During wear, fragrance containing patch 14 is sandwiched and held in place between velcro hook-type cap 36, shoe inner lining such as arch area 44 (as shown in FIG. 6) and velcro loop-type retaining ring 32.

DETAILED DESCRIPTION OF THE INVENTION

For purposes of this invention, the term "shoe" includes any article for the foot to which the deodorizer can be attached, or the insole/deodorizer inserted, such as men's and women's shoes, sneakers, insoles, arch supports, athletic footwear, sandals and the like.

Figure 1A:
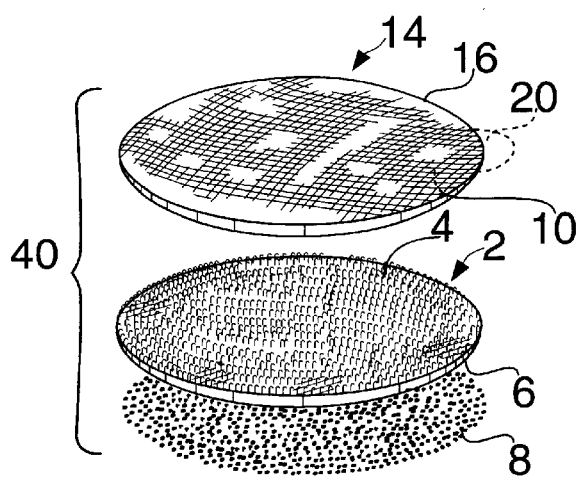
Figure 1B:
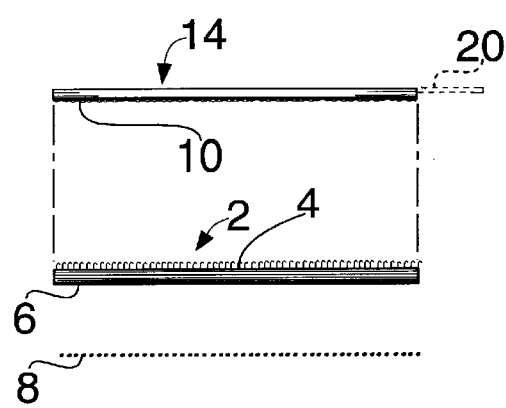
Figure 2A:
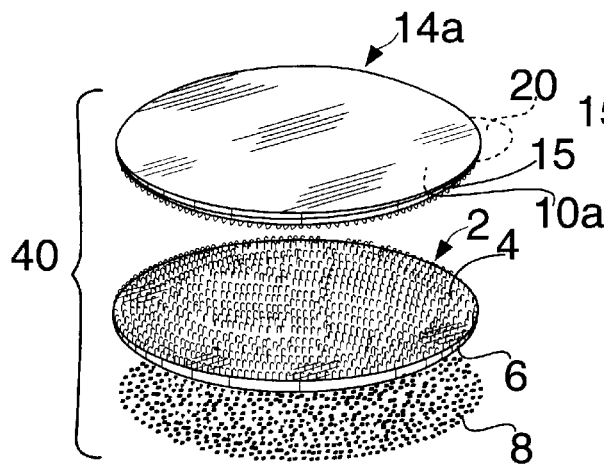
Figure 2B:
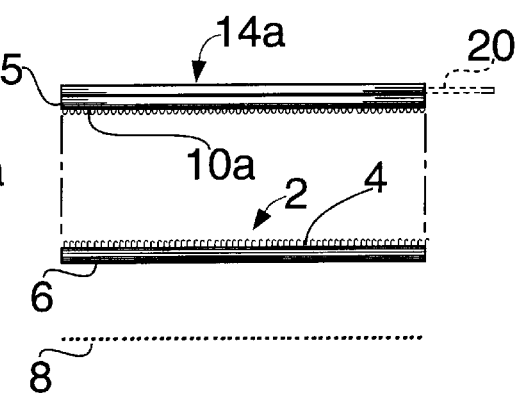
Figure 3A:
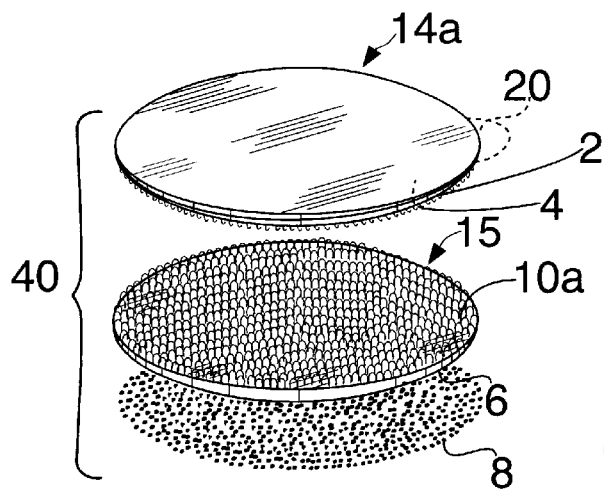
Figure 3B:
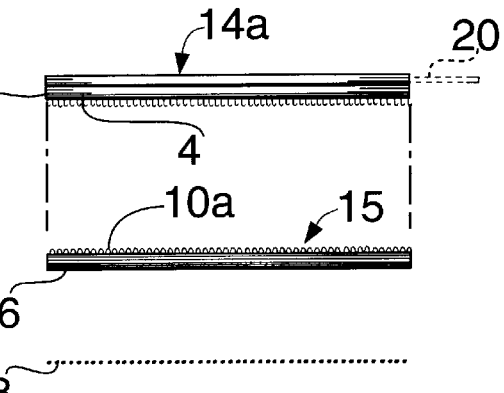
Figures 4A, 4B:
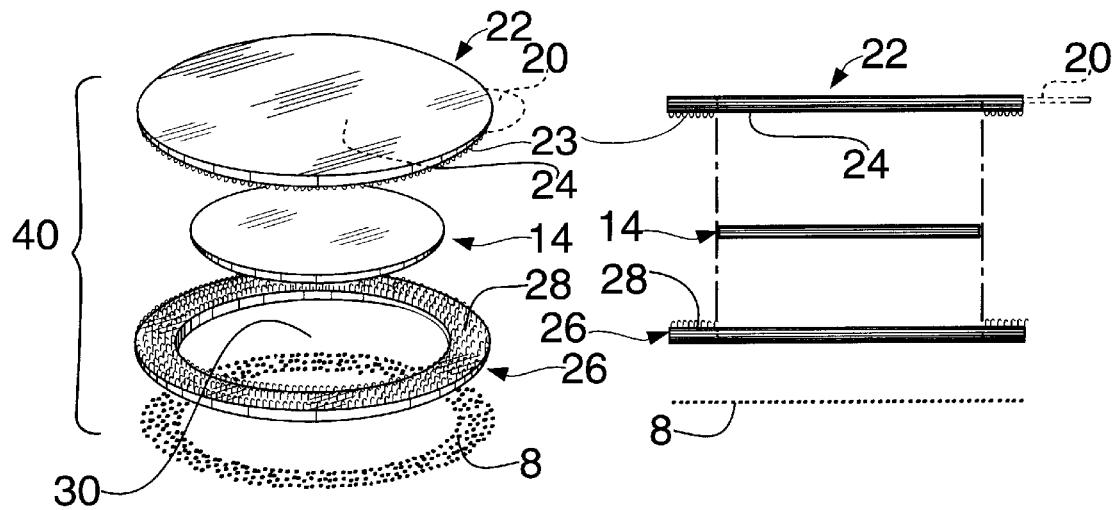
In FIG. 4A and FIG. 4B, deodorizer 40 is made of velcro loop-type cap 22, fragrance containing patch 14, velcro hook-type retaining ring 26 and securing means 8. In this embodiment, fragrance containing patch 14 is inserted into the interior 30 of retaining ring 26, and velcro loop-type cap 22 is placed atop velcro hook-type retaining ring 26. During use, fragrance containing patch 14 is sandwiched and held in place between velcro cap 22, shoe innerlining such as arch area 44 (as shown in FIG. 6) and retaining ring 26. Optionally, velcro loop type cap 22 can also contain tab 20 for facilitating attaching to or removing velcro loop-type cap 22 from velcro hook-type retaining ring 26. The loops 23 on velcro loop-type cap 22 can either partially or completely cover surface 24 of velcro loop-type cap 22. Where partial coverage is used, the loops on velcro loop-type cap 22 can be arranged in any pattern suitable for facilitating intermeshing cap 22 with velcro hook-type retaining ring 26. For example, in FIG. 4A and B, the loops are arranged concentrically around the periphery of cap 22. Also optionally, velcro loops 23 on velcro loop-type cap 22 can be substituted by any material sufficiently looping or fibrous to permit interlocking or intermeshing with velcro hook-type velcro hook-type retaining ring 26. Fragrance containing patch 14 can have a diameter or width about equal to or less than the interior diameter or width of retainer ring 26, to permit convenient insertion into the interior 30 of velcro hook-type retaining ring 26.
Figures 5A, 5B:
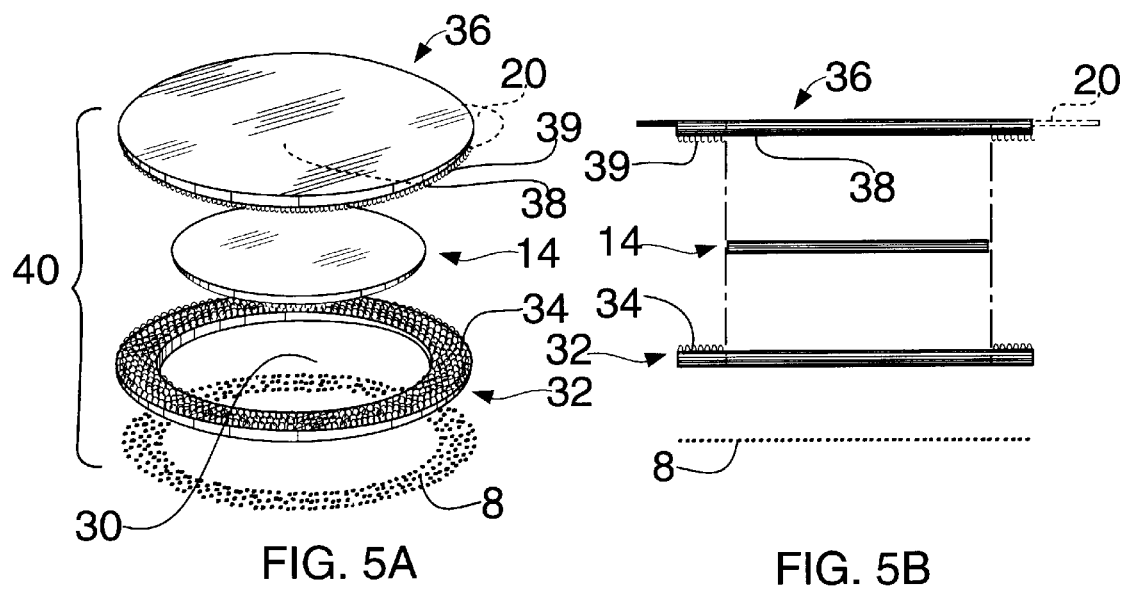
Figure 6:
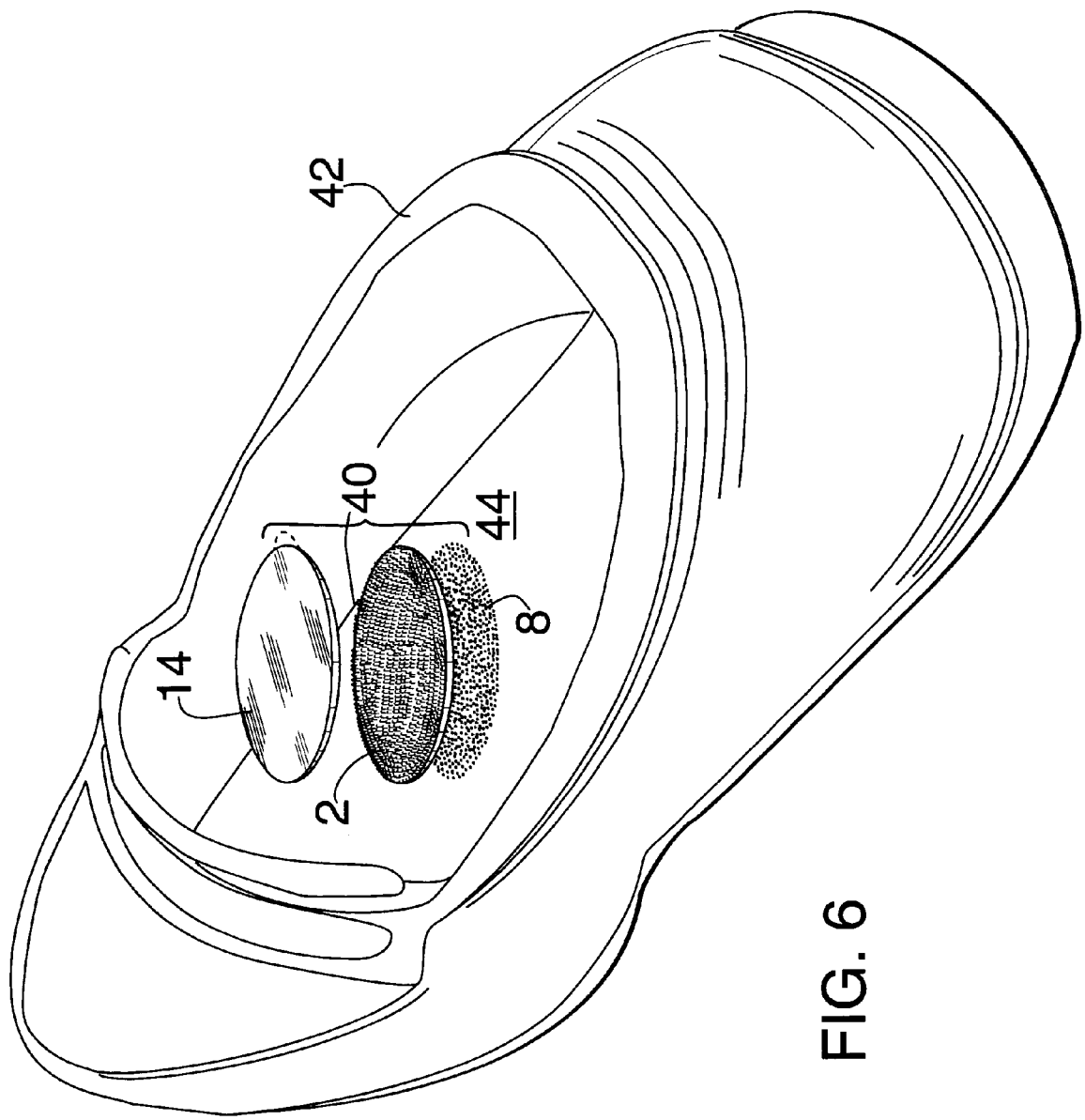
In FIG. 6 is depicted the placement of deodorizer 40 into the interior of shoe 42. Deodorizer 40 is made of fragrance containing patch 14, velcro hook-type fastener 2 and pressure sensitive adhesive 8. Velcro hook-type fastener 2 is bonded to arch area 44 of shoe 42 via adhesive 8 on the underside of fastener 2. Fragrance containing patch 14 is releasably attached and removed from fastener 2.

The deodorizer, retainer and/or patch can be formed into any convenient 2-dimensional geometric shape or aesthetic design, such as circles, ovals, squares, triangles, stars, flowers, animal-shapes, baseballs, basketballs, soccer balls, footballs, hockey pucks, faces, characters and the like. The patch can be of a circular shape or disk-shaped, about 2 to 3 centimeters (cm) in diameter. The individual components of the deodorizer, ie. the patch, cap, fastener, retaining ring, and/or securing means, can be made to any suitable thickness, such from about 1 to about 5 millimeters, more preferably about 2 to 3 millimeters thickness. Similarly, the deodorizer, retaining ring, cap or patch can be covered with any materials which provide a suitable design or illustration, to enhance the appearance of the deodorizer. Either one or both surfaces of the patch can be a loop or fibrous type material, as illustrated in FIGS. 1A–5A. Alternatively, the patch can be made of a material suitable for containing the fragrance wherein the fragrance-containing material is bonded to a velcro-loop type material, as illustrated in FIGS. 2A and 2B.

The fastener, retaining ring or cap are the structural components of the deodorizer which retains or holds the fragrance-containing patch in place. The fastener, retaining ring or cap can be made from any suitable material which can be used to provide for velcro hooks or loops. The fastener or retaining ring can be secured to the shoe interior by any securing means, such as by stitching, staples or adhesives, preferably a pressure sensitive adhesive.

The fragrance containing patch typically comprises a carrier, fragrance and polymer. The carrier is the structural component of the fragrance-containing patch which supports or carries the fragrance and polymer. The carrier can be made of fibrous materials including polypropylene felt, woven and non-woven materials, fabrics, microporous membranes (diffusion loaded), fused microcapsules (encapsulated), monolith films (cast blends of polymer and fragrance) or films of polymers which form molecular associations with the fragrance. Suitable microporous membranes include microporous polyethylene films into which fragrances are diffusion loaded. Preferably, the carrier is a non-woven felt of polypropylene fibers forming a thickness of about 20 to about 100 mils thickness, preferably about 50–75 mils thickness. A felt carrier has the advantage of being able to reduce the oily feel imparted by the fragrance as well as providing enhanced surface area for coating with fragrance/polymer matrices. Also preferred is that the carrier is coated with selected polymer/fragrance blends.

Fragrances employed in the present patch can include any commercial or proprietary fragrance, preferably a "baby-powder" fragrance, a citrus fragrance or an herbal fragrance. The amount of fragrance used in each patch should be sufficient to mask foot and shoe odors for about one day to one week. The amount of fragrance can range from about 10 mg to about 80 mg fragrance, preferably about 20 to about 70 mg fragrance, most preferably about 30 to 50 mg of fragrance per patch.

The fragrance can be entrapped into any suitable polymer which can be coated on the carrier. Alternatively, the fragrance can be incorporated into the carrier itself. Where a polymer is employed, suitable polymers include those prepared from poly(vinyl pyrrolidone), acrylics or hydrogels. Polyvinylpyrrolidone (PVP) is a polymer that possesses unusual complexing and colloidal properties and is physiologically inert, as described in The Handbook of Water-Soluble Gums and Resins by Robert L. Davidson, Chapter 21—"Polyvinylpyrrolidone", McGraw-Hill, Inc. (1980), pp 21-1 to 21-21, whose preparative teachings are incorporated herein by reference. Hydrogels can be derived from the interaction of polyvinylpyrrolidone with urethanes, giving a water swellable material which is slippery when wet. The polyvinylpyrrolidone in the hydrogel is capable of forming complexes with polar materials by hydrogen bonding and can form stable complexes with hydrophobic materials by van der Waals interactions. A commercially available hydrogel is Hydromer®, trademark of Hydromer Inc., Salem Industrial Park, Whitehouse, N.J. Such hydrogels can form excellent films on the carrier even when blended with fragrance.

Preferably, a mixture of the fragrance and a suitable polymer such as polyvinylpyrrolidone are added to the carrier. The fragrance/polymer mixture increases the viscosity of the fragrance, thus facilitating the application of the fragrance to the carrier. The fragrance/polymer mixture has the additional advantage of retarding the evaporation or release of fragrance from the fragrance patch during storage, thus ensuring that the requisite amount of fragrance will be available for deodorizing foot and shoe odors, particularly after the packaging containing the fragrance patch is opened. The mixture also enables the fragrance to associate with the carrier to give a triggered release, ie. time, heat, moisture and pressure, depending upon the type of carrier employed. For example, the use of polyvinylpyrrolidone can give a moisture-triggered release, where the fragrance associated with the polymer can be displaced by water, thus releasing the fragrance. Other polymers or microencapsulation systems can give a temperature- or pressure-triggered release.

Typically, the fragrance is incorporated into the carrier by blending or mixing the fragrance with a polymer and adding the fragrance/polymer mixture to the carrier. Any suitable solvent can be employed for mixing the fragrance with the polymer, including alcohols such as methanol, ethanol and isopropanol, most preferably methanol. The solvent can be employed in amounts sufficient to solubilize the polymer and can range from about 30 to about 70 percent or more solvent, more preferably about 50 percent solvent.

To construct a moisture-triggered patch, the fragrance is blended into a suitable hydrophilic polymer. The fragrance binds to the hydrophilic polymer, but not as strongly as water would. When the complex is exposed to water, the fragrance is displaced and is free to evaporate to mask unpleasant foot or shoe odors.

Where a pressure sensitive adhesive is employed, the adhesive preferably is strong enough to hold the retaining ring or fastener to the shoe interior for about one week to 1–3 months or more. Adhesives which could be used for the shoe deodorizer patch include but are not limited to the following:

A. Solvent-based acrylic adhesives such as:

Monsanto GMS 737, trademark of Monsanto Corporation, St. Louis, Mo.;

National Starch Durotak 72-9720 and 80-1197, trademark of National Starch & Chemical Corp., Bridgewater, N.J.

Ashland's AROSET 1113-AD-40 and 1085-Z-45, trademark of Ashland Oil Co., Ashland, Ky.

B. Solvent-based rubber adhesives such as:

National Starch 36-6172

C. Acrylic emulsion adhesives such as:

Monsanto GME 2397

Rohm & Haas N580, trademark of Rohm & Haas Co., Philadelphia, Pa.

Unocal 76 RES 9646, trademark of Unocal Corp., Los Angeles, Calif.;

Ashland's AROSET 2022-W-50

D. Adhesive Transfer Tapes such as:

3M F-9465 PC, trademark of 3M Co., St. Paul, Minn.

Avery-Denison MED 1116, trademark of Avery Dennison Corp., Pasadena, Calif.

ARCare 7530, trademark of Adhesive Research Inc., Glen Rock, Pa.; and

RX230U, trademark of Coating Science Inc., Bloomfield, Conn.

A release liner should be used to prevent contamination of the adhesive prior to its contact with the footwear. Suitable release liners include high density polyethylene (HDPE), polyester (ie. Mylar®), polyethylene terephthalate (PET) and the like, preferably 7 mil high density polyethylene film.

The following example is intended to illustrate, but not limit the invention.

EXAMPLE

Preparation of a deodorizer for masking foot and shoe odors through the controlled release of fragrance using releasable interlocking surfaces.

A shoe deodorizer as shown for the alternative embodiment for FIGS. 2A and 2B is constructed as follows. In this embodiment, fragrance containing patch 14a is not utilized. A sheet 3 millimeter (mm) thick containing Velcro loops (the mating portion for interlocking with velcro hook type fastener) is impregnated with a blend of polymer, fragrance and solvent. The polymer is polyvinylpyrrolidone, the fragrance is an herbal fragrance and the solvent is methanol. The fragrance is added in an amount calculated to give a fragrance loading of about 25 milligrams (mg) of fragrance for a disk 1.9 centimeters (cm) (0.75 inch) in diameter and the methanol solvent is allowed to evaporate off. A disk 1.9 cm diameter is die-cut from the impregnated sheet containing the polymer, fragrance and velcro loops.

The hook-type fastener for anchorage to the shoe interior is prepared by laminating a sheet 3 millimeter (mm) thick containing Velcro hooks to a 1 mil thickness pressure sensitive adhesive (Aeroset 1085, Ashland Chemical Company, Ashland, Ohio) on a release liner. The adhesive is applied to the surface of the velcro sheet opposite the velcro hooks. A disk 1.9 centimeters (cm) (0.75 inch) in diameter is die-cut from the sheet containing the laminated adhesive and velcro hooks. The disk shaped hook-type fastener is then adhered onto the arch area of a volunteer's shoe.

The disk shaped loop-type fastener containing the fragrance is pressed against the disk shaped hook-type fastener located in the volunteer's shoe and held in place through the interlocking hooks and loops. The deodorizer effectively masks foot and shoe odors for up to one week. After the fragrance is depleted, the loop-type fastener is released by pulling it away from the anchored hook-type fastener. The depleted loop-type fastener is replaced with a fresh loop-type fastener containing the requisite amount of fragrance.

What is claimed is:

1. A deodorizer comprising:
    a) a patch containing fragrance;
    b) a fastener having means for securing said fastener to a surface; and
    c) means directly attached to said fragrance containing patch and means attached to said fastener providing releasable interlocking surfaces which engage upon pressing together said interlocking surfaces of said patch and said fastener and release upon pulling said surfaces apart.

2. The deodorizer of claim 1 wherein the means providing a releasable interlocking surface for said fragrance-containing patch is a surface containing loops or fibrous material and the means providing a releasable interlocking surface for said fastener contains velcro hooks for interlocking with said loop or fibrous material of said fragrance-containing patch.

3. The deodorizer of claim 1 wherein the means providing a releasable interlocking surface for said fragrance-containing patch is a surface containing velcro hooks and the means providing a releasable interlocking surface for said fastener contains loop or fibrous material for interlocking with said velcro hooks of said fragrance-containing patch.

4. The deodorizer of claim 1 having a circular shape.

5. The deodorizer of claim 1 wherein at least a portion of said patch is made of a carrier containing a mixture of fragrance and polymer binder.

6. The deodorizer of claim 5 wherein the polymer binder is polyvinylpyrrolidone.

7. The deodorizer of claim 5 wherein the carrier is made of a non-woven felt.

8. The deodorizer of claim 7 wherein the non-woven felt is made of polypropylene fibers.

9. The deodorizer of claim 1 wherein the amount of fragrance in the patch ranges from about 10 milligrams to about 80 milligrams.

10. A deodorizer comprising:
    a) a patch containing fragrance in amounts effective to mask foot and shoe odors;
    b) a retaining ring having an opening into which said fragrance-containing patch is inserted into and said retaining ring also having means for securing said retaining ring to a surface;
    c) a cap for maintaining said patch within said retaining ring; and
    d) means attached to said retaining ring and means attached to said cap providing releasable interlocking surfaces which engage upon pressing together said interlocking surfaces of said retaining ring and said cap and release upon pulling said surfaces apart to allow easy insertion and removal of the patch from the deodorizer.

11. The deodorizer of claim 10 wherein the means providing a releasable interlocking surface for said retaining ring is a surface containing velcro hooks and the means providing a releasable interlocking surface for said cap contains loop or fibrous material for interlocking with said velcro hooks of said retaining ring.

12. The deodorizer of claim 10 wherein the means providing a releasable interlocking surface for said retaining ring is a surface containing loops or fibrous material and the means providing a releasable interlocking surface for said cap contains velcro hooks for interlocking with said loop or fibrous material of said retaining ring.

* * * * *